(12) United States Patent
Meron et al.

(10) Patent No.: US 8,640,921 B2
(45) Date of Patent: Feb. 4, 2014

(54) DEVICE, SYSTEM AND METHOD FOR DISPENSING A FIXED DOSE OF FLUID

(75) Inventors: Moti Meron, Herzliah (IL); Aner Tsuk, Mazkeret Batia (IL); Roee Atlas, Givatayim (IL); Israel Nur, Moshav Timmorim (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 109 days.

(21) Appl. No.: 13/209,650

(22) Filed: Aug. 15, 2011

(65) Prior Publication Data

US 2012/0043347 A1 Feb. 23, 2012

(30) Foreign Application Priority Data

Aug. 19, 2010 (IL) .......................................... 207715

(51) Int. Cl.
*B67D 7/70* (2010.01)

(52) U.S. Cl.
USPC .......................................... 222/137; 222/390

(58) Field of Classification Search
CPC ........... A61M 5/24; A61M 5/315; B67D 7/60
USPC .............. 222/137, 390, 391, 326, 325, 145.5; 604/194, 224, 234, 209, 214
See application file for complete search history.

(56) References Cited

U.S. PATENT DOCUMENTS

| | | | | |
|---|---|---|---|---|
| 1,823,654 A | * | 9/1931 | Hast | ................................ 222/52 |
| 2,725,877 A | * | 12/1955 | Reiter et al. | .................. 604/135 |
| 3,952,920 A | | 4/1976 | Bergman | |
| 4,306,671 A | * | 12/1981 | Fisher | .......................... 222/326 |
| 5,161,715 A | | 11/1992 | Giannuzzi | |
| 5,814,022 A | | 9/1998 | Antanavich et al. | |
| 6,113,571 A | | 9/2000 | Zinger et al. | |
| 6,234,994 B1 | | 5/2001 | Zinger | |
| 6,464,663 B1 | | 10/2002 | Zinger | |
| 6,565,539 B1 | | 5/2003 | Zinger et al. | |
| 7,959,612 B2 | * | 6/2011 | Thompson et al. | ........... 604/191 |
| 8,192,198 B2 | * | 6/2012 | An | .................................. 433/89 |
| 2008/0103564 A1 | | 5/2008 | Burkinshaw et al. | |
| 2009/0264831 A1 | | 10/2009 | Thompson et al. | |
| 2010/0143864 A1 | | 6/2010 | An | |
| 2012/0148980 A1 | * | 6/2012 | Gramann | ........................ 433/90 |

FOREIGN PATENT DOCUMENTS

| | | |
|---|---|---|
| EP | 1113839 | 11/2004 |
| EP | 1845860 | 3/2009 |
| WO | WO 2008/101829 | 8/2008 |
| WO | WO 2010/150396 | 12/2010 |

OTHER PUBLICATIONS

International Search Report re: PCT/IL2011/000663 dated Jan. 4, 2012.

* cited by examiner

*Primary Examiner* — Lien Ngo
(74) *Attorney, Agent, or Firm* — David R. Crichton (57) ABSTRACT

The invention relates to a device for dispensing a fixed dose of fluid, the device comprising at least one barrel; at least one plunger at least partially enclosed within the barrel; a motion conversion mechanism for transferring actuated pressure force applied outside the barrel into movement of the at least one plunger in a dispensing direction, wherein the motion conversion mechanism comprises at least one rotating gear; and a releasing mechanism for disconnecting the plunger from the motion conversion mechanism, wherein at a released position the at least one plunger can move in a direction opposite to the dispensing direction, independent of a rotational movement of the at least one gear, and wherein the movement of the plunger in the opposite direction to the dispensing enables loading the fluid into the barrel.

27 Claims, 11 Drawing Sheets

DEVICE, SYSTEM AND METHOD FOR DISPENSING A FIXED DOSE OF FLUID

CROSS REFERENCE TO RELATED APPLICATIONS

The present application claims the benefit of Israeli Application Number IL 207715, filed Aug. 19, 2011.

FIELD OF THE INVENTION

The invention relates to devices and systems for dispensing fluids and methods of using the same.

BACKGROUND OF THE INVENTION

Medical devices for administering fluids either by injection, spraying or dripping are basically known. In particular, medical devices for administering at least two components such as fibrinogen and thrombin are known from U.S. Pat. No. 6,565,539; U.S. Pat. No. 6,464,663; U.S. Pat. No. 6,234,994; U.S. Pat. No. 6,113,571; EP 1,845,860; EP 1113839; U.S. Pat. No. 3,952,920; U.S. Pat. No. 5,161,715; U.S. Pat. No. 5,814,022; and US 20090264831.

The devices disclosed in the above documents don't provide an easy to use solution for administering multiple, sequential and predetermined doses of fluids.

There is a need for a device for administering fluids wherein the disadvantages of the prior art are overcome.

SUMMARY OF THE INVENTION

The invention provides a device for dispensing a fixed dose of fluid. The device comprising: at least one barrel (42), at least one plunger (27) at least partially enclosed within the barrel (42), a motion conversion mechanism (M1) for transferring actuated pressure force applied outside the barrel into movement of the at least one plunger (27) in a dispensing direction, wherein the motion conversion mechanism comprises at least one rotating gear; and a releasing mechanism (R1) for disconnecting the plunger from the motion conversion mechanism, wherein at a released position the at least one plunger (27) can move in a direction opposite to the dispensing direction, independent of a rotational movement of the at least one gear, and wherein the movement of the plunger (27) in the opposite direction to the dispensing enables loading the fluid into the barrel (42).

According to some embodiments of the present invention the motion conversion mechanism comprises at least one rack gear (43), at least one pinion gear (3) and at least one rotatable cylindrical threaded shaft (36) connected directly or indirectly to the at least one plunger (27), wherein the releasing mechanism disconnects the plunger from the cylindrical threaded shaft (36).

According to some embodiments of the present invention the releasing mechanism comprises a split nut (26) attached to the at least one plunger (27), wherein the split nut engages the cylindrical threaded shaft and rotates along the cylindrical threaded shaft (36) and the operation of the releasing mechanism comprises opening the split nut to enable free movement of the plunger.

According to some embodiments of the present invention the releasing mechanism further comprises a splitting element (50), wherein the split nut (26) is composed of two parts connected via a pivot (44) and has an opened and closed position, such that when the splitting element is moved along the barrel axis during the loading, the split nut is opened by the splitting element.

According to some embodiments of the present invention the splitting element is part of a bar (33) having a fork-like channel structure (47), wherein the bar is connected to a pulling handle (30), wherein the split nut is composed of two parts connected via a pivot connection (44) and the bar is associated with the two parts of the split nut such that the movement of the bar caused by pulling the handle (30) pushes the split nut parts apart in the fork-like channel, thereby opening the split nut (26).

According to some embodiments of the present invention the device further comprises an actuating handle (20) located outside the barrel and rack (43) and pinion (3) gears which convert a linear movement of the handle (20) into the rotational movement of the cylindrical threaded shaft (36).

According to some embodiments of the present invention at each actuation operation the fixed dose is determined by the pitch of the cylindrical threaded shaft (36) and the diameter of the barrel (42).

According to some embodiments of the present invention the rack (43) gear is connected to the rotatable cylindrical threaded shaft (36) by two opposite crown gears (2A, 2B) enabling rotation of the cylindrical threaded shaft (36) only in one direction.

According to some embodiments of the present invention the crown gears (2A, 2B) design forms small gaps between the gear's teeth preventing backwards movement of the plunger (27) throughout the motion conversion mechanism operation.

According to some embodiments, the present invention provides a device for dispensing a fixed dose of fluid, the device comprises: at least one barrel (42); at least one plunger (27) at least partially enclosed within the barrel (42); a motion conversion mechanism (M1) for transferring actuated pressure force applied outside the barrel (42) into movement of the at least one plunger (27) in a dispensing direction, wherein the motion conversion mechanism comprises at least one rotating gear; and a releasing mechanism (R1) for disconnecting the plunger from the motion conversion mechanism, wherein at a released position the at least one plunger (27) can move in a direction opposite to the dispensing direction independent of a rotational movement of the at least one gear, wherein the movement of the plunger in the opposite direction enables loading the fluid into the barrel, wherein the motion conversion mechanism (M1) comprises at least one rack gear (43), at least one pinion gear (3), and at least one rotatable cylindrical threaded shaft (36) connected directly or indirectly to the at least one plunger, wherein the releasing mechanism (R1) disconnects the plunger (27) from the cylindrical threaded shaft (36), wherein the releasing mechanism comprises a split nut (26) attached to the at least one plunger (27) and engages the cylindrical threaded shaft (36), wherein the split nut (26) rotates along the cylindrical threaded shaft (36) and the operation of the releasing mechanism (R1) comprises opening the split nut (26) to enable free movement of the plunger (27) in the opposite direction.

According to some embodiments, the present invention provides a system for dispensing a fixed dose of two fluids and creating a mixed composition of the two fluids, the system comprises: a housing (1) enclosing two cylindrical cavities forming two barrels (42a and b), two plungers (27) at least partially enclosed within the barrels (42a and b), a motion conversion mechanism (M1) for transferring actuated pressure force applied outside the housing into movement of the plungers (27) in a dispensing direction, wherein the motion conversion mechanism comprises at least one rack gear (43), at least one pinion gear (3) and at least one rotatable cylindrical threaded shaft (36) connected with the two plungers (27), a releasing mechanism (R1) for disconnecting the two plungers (27) from the rotatable cylindrical threaded shaft (36), wherein at a released position the plungers can move in an opposite direction to the dispensing direction independent of the rotational movement of the motion conversion mechanism (M1); and two nozzles (9) for each barrel connected to an outlet opening (39) of the system, wherein the fluids pass from the barrels (42) through the nozzles (9) into the outlet opening (39) of the system.

According to some embodiments of the present invention, the system comprises a split nut (26) attached to the two plungers (27) and engages the cylindrical threaded shaft (36), wherein the split nut (26) rotates along the rotatable cylindrical threaded shaft (36) and the operation of the releasing mechanism (R1) comprises opening the split nut (26) to enable free movement of the plungers (27).

According to some embodiments of the present invention, the releasing mechanism comprises a pulling handle (30) connected to a bar (33) having fork-like channel structure (47), wherein the split nut (26) is composed of two parts connected via a pivot connection (44) and the bar is associated with the two parts of the split nut (26) such that the movement of the bar caused by pulling the handle (30) pushes the split nut parts apart in the fork-like channel, thereby opening the split nut (26).

According to some embodiments of the present invention, the system further comprises an actuating handle (20) located outside the housing (1), and rack (43) and pinion (3) gears which convert a linear movement of the handle (20) into the rotational movement of the cylindrical threaded shaft (36).

According to some embodiments of the present invention, at each actuation operation the fixed dose is determined by the pitch of the cylindrical threaded shaft (36) and the diameter of the barrels (42).

According to some embodiments of the present invention, the rack (43) and pinion (3) gears are connected to the rotatable threaded shaft (36) by two opposite crown gears (2A, 2B) enabling rotation of the cylindrical threaded shaft (36) only in one direction.

According to some embodiments of the present invention, the crown gears design forms small gaps between the gear teeth preventing backwards movement of the plunger (27) throughout the motion conversion mechanism operation.

According to some embodiments, the present invention provides a method for loading and dispensing a fluid, the method comprising the steps of: moving an at least one plunger (27) through an at least one barrel (42) in a dispensing direction by transforming pressure applied outside the at least one barrel into a linear movement of the at least one plunger in the dispensing direction, the transformation achieved through a rotational movement of a motion conversion mechanism (M1), disconnecting the at least one plunger (27) from the motion conversion mechanism (M1) for moving the at least one plunger (27) in a direction opposite to the dispensing direction independent of the rotational movement of the motion conversion mechanism, wherein the movement of the at least one plunger (27) in the opposite direction enables loading the fluid from a connected reservoir into the at least one barrel (42).

According to some embodiments of the present invention, the rotational movement comprises rotation of a split nut (26) along a rotatable cylindrical threaded shaft (36), wherein the split nut (26) is directly or indirectly connected to the at least one plunger and the cylindrical threaded shaft is part of the motion conversion mechanism.

According to some embodiments of the present invention the disconnecting comprises opening the split nut (26) to enable free movement of the at least one plunger (27) for loading the at least one barrel (42) with the fluid.

According to some embodiments of the present invention the method further comprises the step of closing the split nut (26) to reconnect the at least one plunger (27) to the cylindrical threaded shaft (36) for enabling the dispensing operation.

According to some embodiments of the present invention, the opening and loading further comprises pulling a handle (30) connected to a bar (33) having a fork-like channel structure, wherein the split nut (26) is composed of two parts connected via a pivot connection (44) and the fork-like channel structure is associated with the two parts of the split nut such that the movement of the fork-like channels structure, caused by pulling the handle (30), pushes the parts apart, thereby opening the split nut (26).

According to some embodiments of the present invention, the rotational movement is achieved by converting a linear movement of a handle (20) into the rotational movement using a rack (43) and pinion (3) gears.

According to some embodiments of the present invention, the rack (43) and pinion (3) gears are connected to the rotatable threaded shaft (36) by two opposite crown gears (2A, 2B) enabling rotation only in one direction.

According to some embodiments of the present invention, the dispensing is selected from the group consisting of injecting, spraying and dripping.

According to some embodiments of the present invention, the ratio between the diameters of the two barrels is correlated to the required ratio between the two fluids.

According to some embodiments of the present invention, the split nut (26) has a pair of bulges (45) attached at the end of each part of the split nut (26), the bulges are designed to slide in the channels (45, 46) of the spread bar (33) for opening or closing the split nut (26).

According to some embodiments, the present invention provides a device for dispensing a liquid comprising: at least one barrel (42), at least one plunger (27) which can be disposed within the at least one barrel (42), a rotatable cylindrical threaded shaft (36), a split nut (26) connected directly or indirectly to the at least one plunger (27) and having an opened position and a closed position, wherein the split nut (26) engages the threaded shaft (36) in the closed position and is disengaged from the threaded shaft in the opened position, when the split nut (26) is in the closed position, rotation of the threaded shaft translates into a linear movement of the split nut (26) and the at least one plunger (27) in a dispensing direction, and when the split nut (26) is in the opened position it disengages from the threaded shaft (36), thereby allowing the at least one plunger (27) to move opposite to the dispensing direction.

According to some embodiments of the invention, the two fluids are a thrombin component and a fibrinogen component.

BRIEF DESCRIPTION OF THE DRAWINGS

The parts, aspects, and advantages of the present invention will become better understood with regard to the following description, examples, claims, and the following figures.

FIG. 10 illustrates the fluid path in the front end of the device.

DETAILED DESCRIPTION OF THE INVENTION

In one aspect, the invention relates to a device for dispensing a liquid comprising: a barrel (42); a plunger (27) which can be disposed within the barrel; a rotatable cylindrical threaded shaft (36); and a split nut (26) connected directly or indirectly to the plunger. The split nut may be in an opened position or in a closed position. The split nut engages the threaded shaft in the closed position and is disengaged from the threaded shaft in the opened position. In one embodiment of the invention, when the split nut is in the closed position, rotation of the threaded shaft translates into a linear movement of the split nut and the plunger in a dispensing direction, and when the split nut is in the open position it disengages from the threaded shaft and thus the plunger can move opposite to the dispensing direction (e.g. a loading direction).

The device may comprise more than one barrel and corresponding plunger. According to some embodiments of the present invention the device includes two plungers integrated by a fitting structure, enabling unison movement of both plungers, such structure may be a plunger base 32.

According to some embodiments of the present invention, the device is suitable for administering a predetermined dose of at least one fluid e.g. two therapeutic fluids such as a fluid fibrinogen component and a fluid thrombin component. The device can be used for simultaneously administering the two therapeutic fluids. The device may also be used for simultaneously administering the therapeutic fluids and a cell suspension. In such an embodiment, the cells can be formulated with the fibrinogen component, the thrombin component and/or can be administered as a separated component. The administration can be carried out by injection e.g. when a needle is installed on the outlet of the device (see 39 in FIG. 1), by dripping, or by spraying (e.g. when a gas outlet e.g. a pressurized gas is added to the dispensing end of the device). As shown in FIGS. 1, 2, 3, and 4A-B, in one embodiment of the invention, the device assembly comprises the following parts: a housing (48)—which integrates three housing elements: a first housing element (28); a second housing element (1) which encloses two cylindrical cavities, each cavity functioning as a barrel (see 42a and b in FIGS. 4A-B) for one plunger (27); and a third housing element (11) having a male luer connection type. The male luer connection can be adapted for placing a needle.

Figure 2:
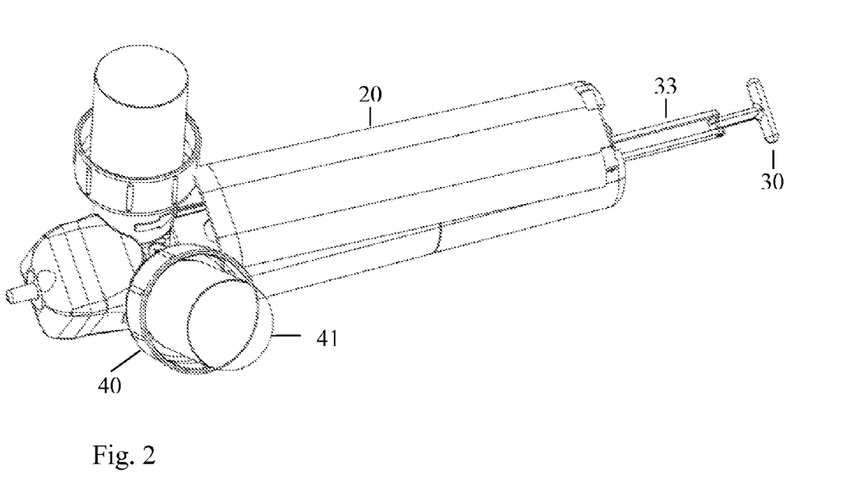

In one embodiment of the invention, an actuating handle (20) is connected on one end to the first housing element (28) and on the other end to a retractable actuating mechanism (18) installed on the third housing element (11), conveying a linear movement of the handle 20 (in direction V2) to a rotational movement of the rotatable cylindrical threaded shaft (36) for moving the plungers (27) in a linear movement in the direction V4. In one embodiment of the invention, on the surface of the third housing element (11), a fluid control device (6) is installed as described in PCT patent application NO. WO9810703. The fluid control device (6) is designed to connect at least one spike cup (40) with a vial/reservoir (41) for filing the barrel with the required fluid (a spike cup and a vial connected to the third housing element (11) is shown in FIG. 2).

Figure 3:
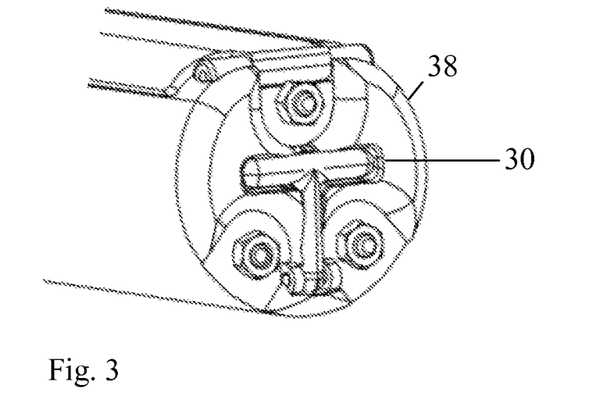
FIG. 3: illustrates a back view of the device wherein pulling handle 30 is situated according to some embodiments of the present invention.

FIG. 3 illustrates a back view of the device according to some embodiments of the present invention. A pulling handle (30) is provided for pulling the at least one plunger backwards e.g. in a loading direction opposite to the dispensing direction. The pulling handle (30) is connected to a spread bar (33; see FIG. 2 and in FIG. 16). In one embodiment, the bar is located within the void of the first housing (28).

Figure 4A:
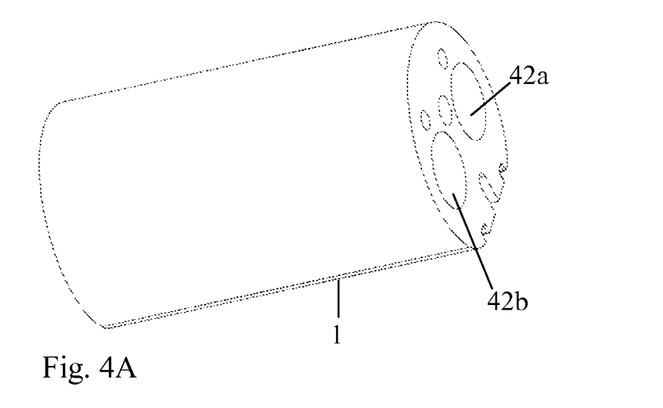
FIGS. 4A-4B: illustrate an embodiment of a second housing (1); (also shown in FIG. 1) enclosing two cylindrical cavities (42a and b) forming two barrels according to some embodiments of the present invention.
Figure 4B:
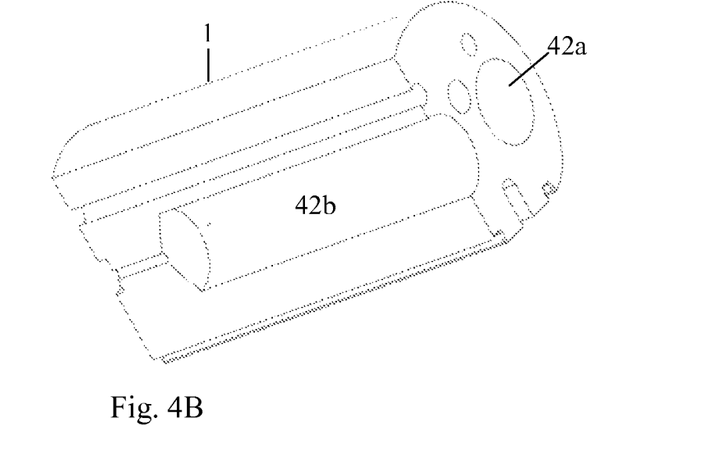

FIGS. 4A and 4B illustrate the inner structure of the second housing element (1) wherein inner cavities 42a and 42b function as barrels according to some embodiments of the present invention.

Figure 5:
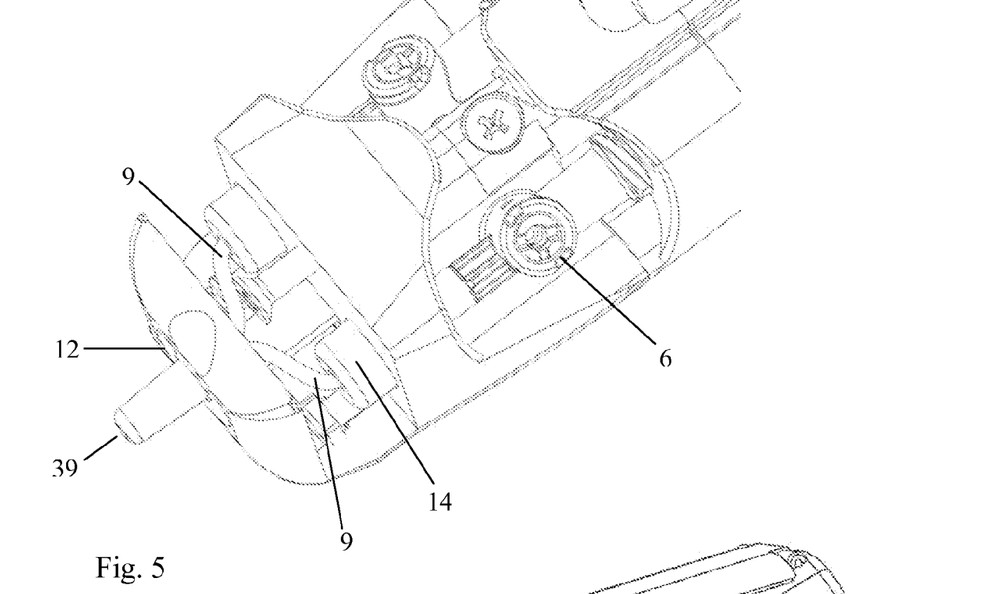
FIG. 5: illustrates the front end of the device according to some embodiments of the present invention.
Figure 10:
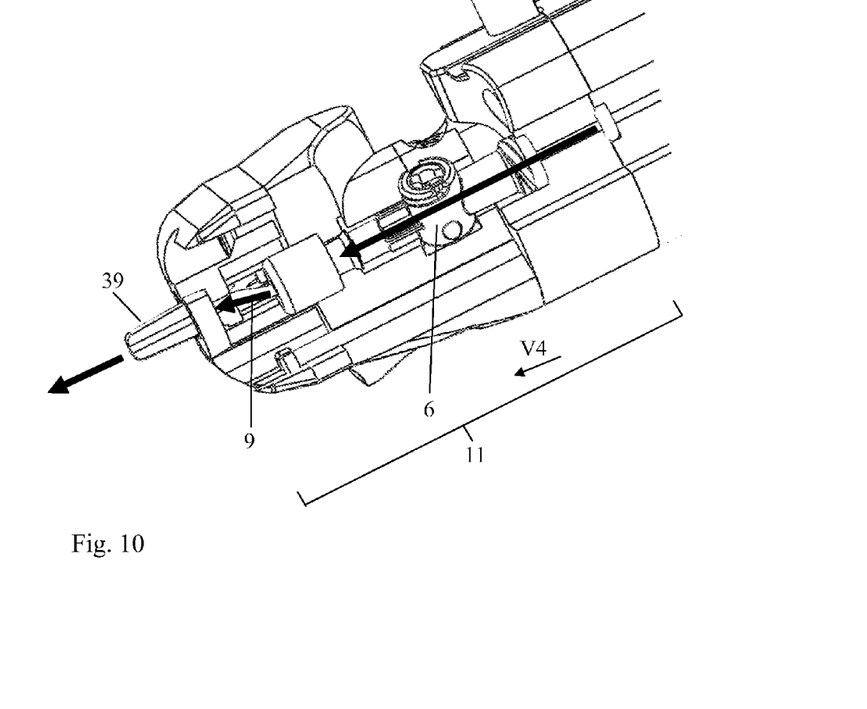

FIGS. 5 and 10 illustrate the inner structure of the third housing element (11) according to some embodiments of the present invention. At the front of the housing (11) is installed an outlet nozzle (39) partly protruding from the housing element (11). In one embodiment of the invention, the outlet nozzle (39) is made from a rigid material such as plastic. The nozzle (39) is connected with the front end of the barrels (42a and b) through flexible nozzles (9), the adaptors (14) and the fluid control devices (6). In one embodiment of the invention, an injection needle (not shown) is installed on the rigid outlet nozzle (39). In another embodiment of the invention, the injection needle is disposable and may be replaced. In one embodiment of the invention, the needle may be disposed off automatically by a needle ejector (12) which is associated with the outlet nozzle (39). In these figures the upper part of the fluid control device (6) is shown, revealing the connection interface having a designated structure for connecting with the spike cups (40).

Figure 6:
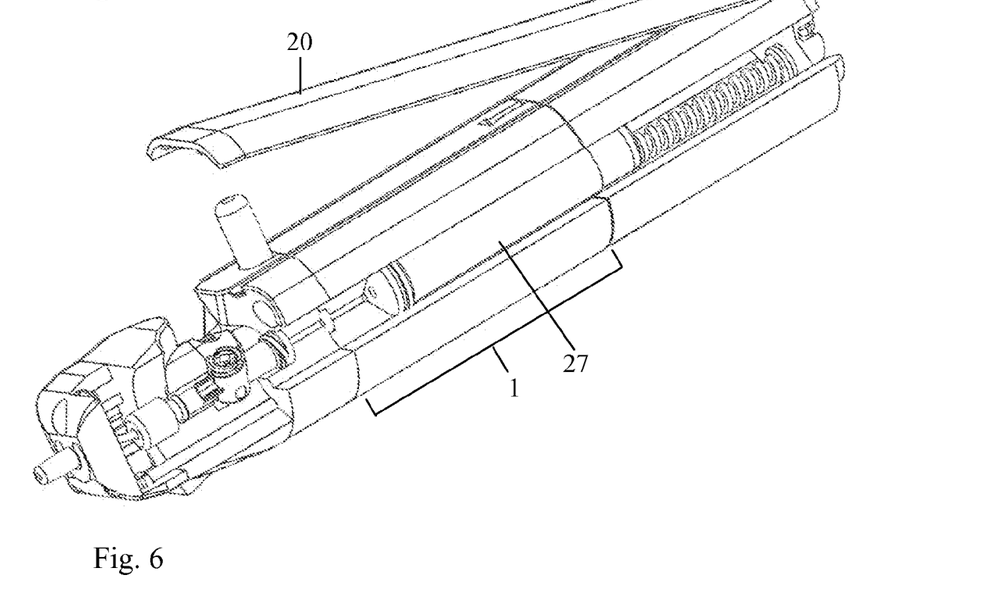
FIG. 6: illustrates an initial state of the device wherein the plungers (27) are located within the barrels close to the front end of the second housing (1) according to some embodiments of the present invention.

FIG. 6 illustrates some of the inner parts of the device according to some embodiments of the present invention. The plungers (27) are shown in their "pushed" position within cavities 42a and b (the cavities are shown best in FIG. 4A) of the second housing element (1). The first housing element (28) comprises the threaded part of the rotatable cylindrical threaded shaft (36), which enables the movement of the plungers (27) into the barrels.

Figure 7:
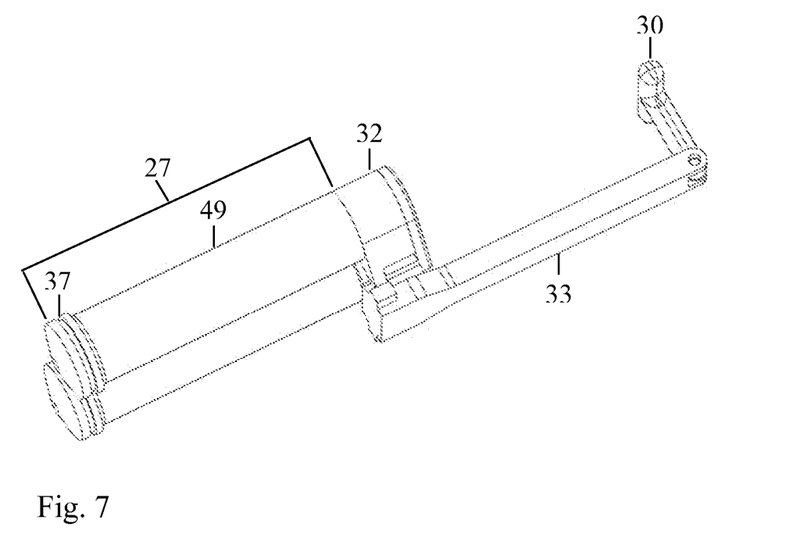
FIG. 7: illustrates the connection between the pulling handle (30) and a plunger base (32) according to some embodiments of the present invention.

FIG. 7 illustrates the parts of the plungers (27) according to some embodiments of the present invention. Each plunger is comprised of a body (49) and plunger head (37). The plungers are indirectly associated with spread bar 33 which in turn is attached to the pulling handle (30). The association is carried out via a plunger base (32) that connects the two plungers so that they move in unison with each other.

Figure 8:
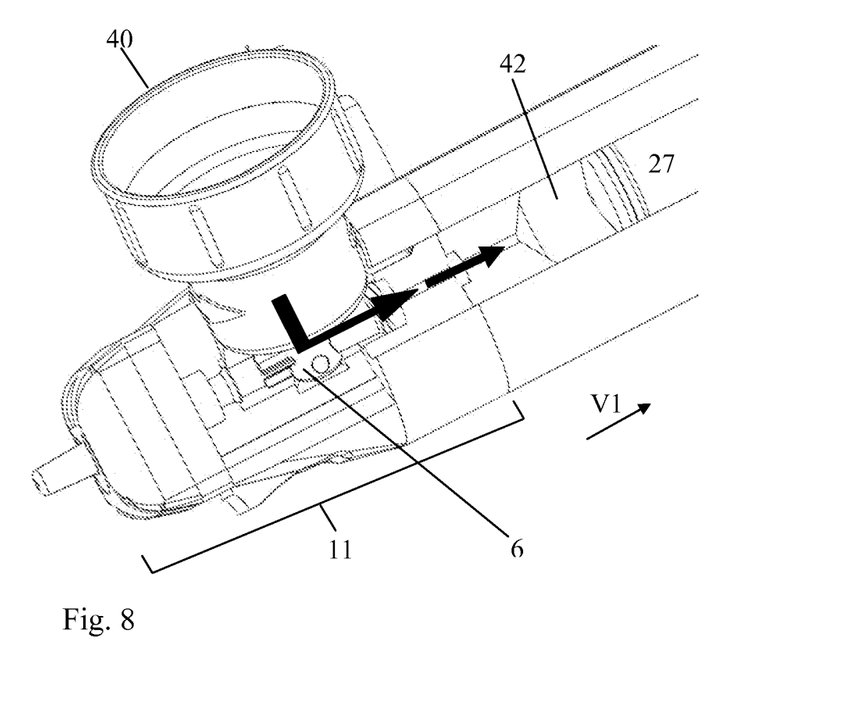
FIG. 8: illustrates the fluid path during loading of the device from vials located within the spike cups (40) and into the barrels (42) according to some embodiments of the present invention.

FIG. 8 illustrates a spike cup (40) connected to the third housing element (11) via a fluid control device (6) according to some embodiments of the present invention. The spike cups (40) are associated (e.g. in fluid communication) with barrels (42) through the fluid control device (6), enabling to control feeding of the fluid through the spike cusp (40) and into the barrels (42).

Figure 9:
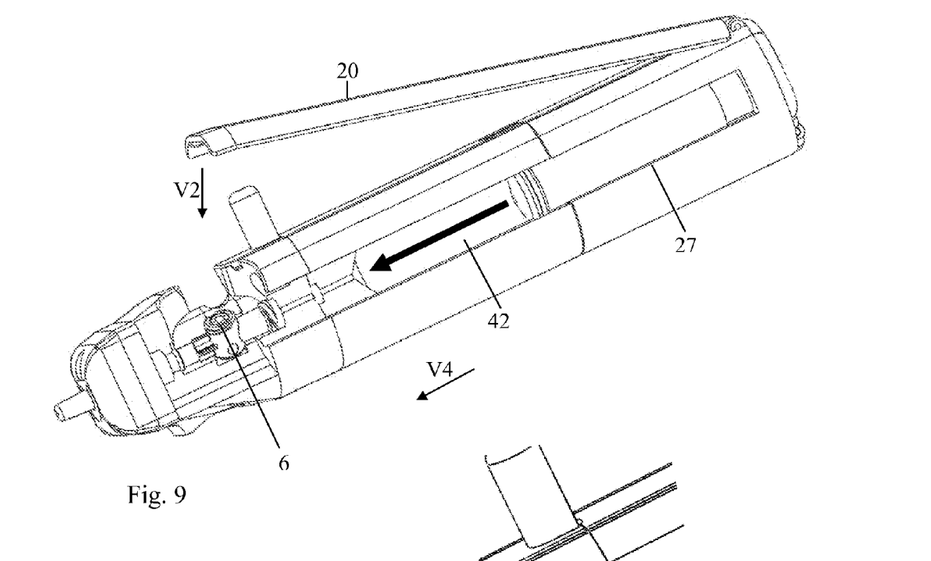
FIGS. 9-10: illustrate an embodiment of the fluid path during actuation of the handle (20) according to some embodiments of the present invention.

FIG. 9 illustrates inner parts of the device according to some embodiments of the present invention. The plungers (27) are in their "open position" [drawn from the barrels (42)], and are movable along the barrels towards the front part of the housing 1 (in direction V4).

Figure 11:
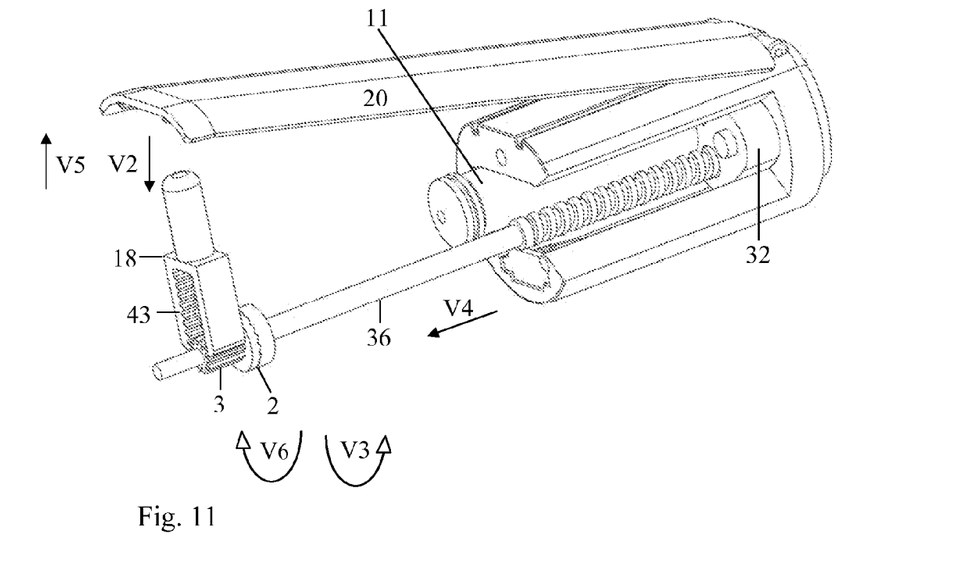
FIGS. 11-12: illustrate parts in the device that are involved, inter alia, in the liquid dispensing step according to some embodiments of the present invention.
Figure 12:
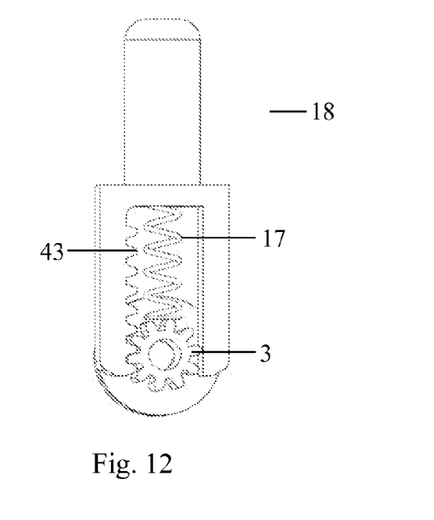

FIGS. 11 and 12 illustrate inner parts of the motion conversion mechanism which convert the linear movement of the actuating handle (20) into a rotational movement of the rotatable cylindrical threaded shaft (36), and back to a linear movement of the plungers (27). In a first phase, the motion conversion mechanism converts a linear movement of the actuating handle (20) into a rotational movement of the threaded shaft (36). In one embodiment of the invention, the motion conversion mechanism comprises a rack gear (43), a pinion gear (3), a rotatable cylindrical threaded shaft (36), crown gears (2A, 2B—see FIG. 14), a plunger base 32, and split nut (26). In reaction to the activation of the actuating handle (20), push slide 18 moves in the same direction V2, the rack gear (43) is pushed down (in direction V2), and the pinion gear (3) is rotated (in direction V3). The pinion gear (3) is mounted on the rotatable cylindrical threaded shaft (36) and is connected to a crown gear mechanism (2A, 2B). The crown gear mechanism transfers the rotational motion in only one direction to the cylindrical threaded shaft (36) for moving the plungers (27) forward (in direction V4) in a second phase of the motion conversion mechanism. The crown gear mechanism is illustrated in FIG. 14.

Figure 13A:
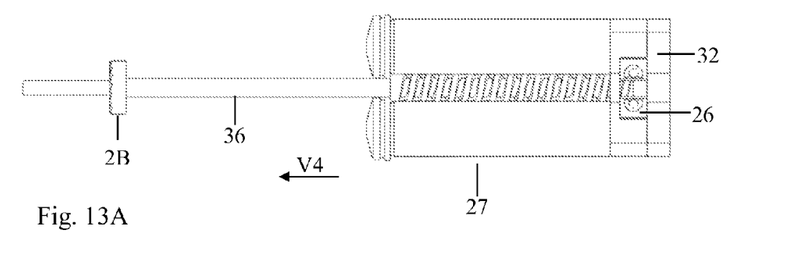
FIGS. 13A-13B: illustrate the plunger base (32) positioned at two different points along the cylindrical threaded shaft (36), illustrating the movement of the plungers (27) along the cylindrical threaded shaft (36) according to some embodiments of the present invention.
Figure 13B:
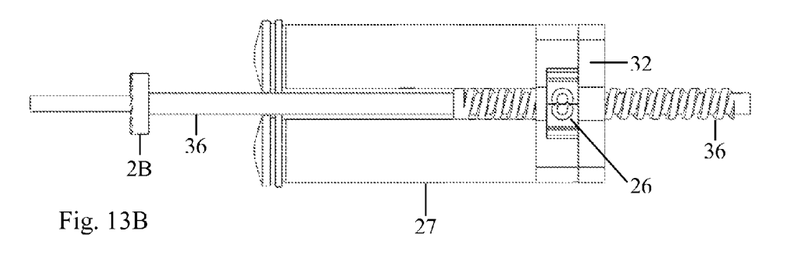

FIGS. 13A and B illustrate the plunger base (32) positioned at two different points along the cylindrical threaded shaft (36) and some parts of the motion conversion mechanism (M1)—crown 2B that is mounted on the threaded shaft (36) which in turn is connected with the split nut (26). The split nut (26) is located within the plunger base (32) and thus is associated with the plungers (27). The plunger base (32), the split nut (26) and the plungers move along the threaded shaft (36) in the same direction V4. In FIG. 13A the plunger base (32) and the split nut (26) (located within the plunger base) are situated at the back side of the first housing (28); and in FIG. 13B the plunger base with the split nut (26) is located at a lower position following the movement of the split nut along the threaded shaft (36) in the direction V4. The term "motion/movement conversion mechanism (M1)" is interchangeable with the term "gearing mechanism".

Figure 14:
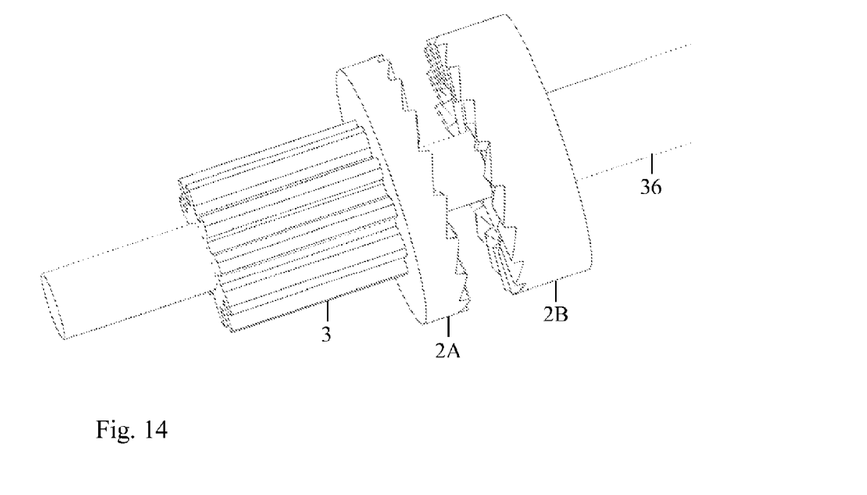
FIG. 14: illustrates the engagement between the pinion gear (3) and the rotatable cylindrical threaded shaft (36; also illustrated in FIG. 13) according to some embodiments of the present invention.

FIG. 14 illustrates the crown gear mechanism (2A, 2B) according to some embodiments of the present invention. The crown gear parts 2A and 2B are designed with specific orientation of the teeth to allow rotation only in one direction (FIG. 11, V3), preventing movement of the plunger in the direction V1 while the actuating handle (20) returns upwards. The space between the teeth is designed to enable minimal rotation in the opposite direction (V6) and minimal backward movement of the plungers (27) while the actuating handle (20) returns upwards.

The device according to some embodiments of the present invention comprises a releasing mechanism (R1) enabling to disconnect the plunger base (32) from the cylindrical threaded shaft (36), enabling the plungers to move backward freely (in V1 direction) independently of the rotational movement of the cylindrical threaded shaft. The releasing mechanism may comprise split nut 26 and spread bar 33 as further described below.

Figure 15A:
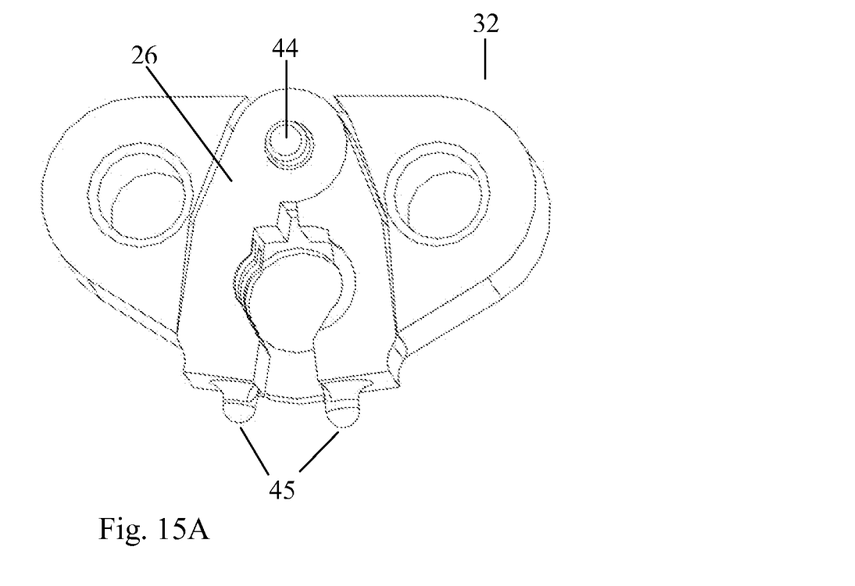
FIGS. 15A-15B: illustrate an opened (A) and closed (B) position of the split nut (shown in FIG. 13, part 26) according to some embodiments of the present invention.
Figure 15B:
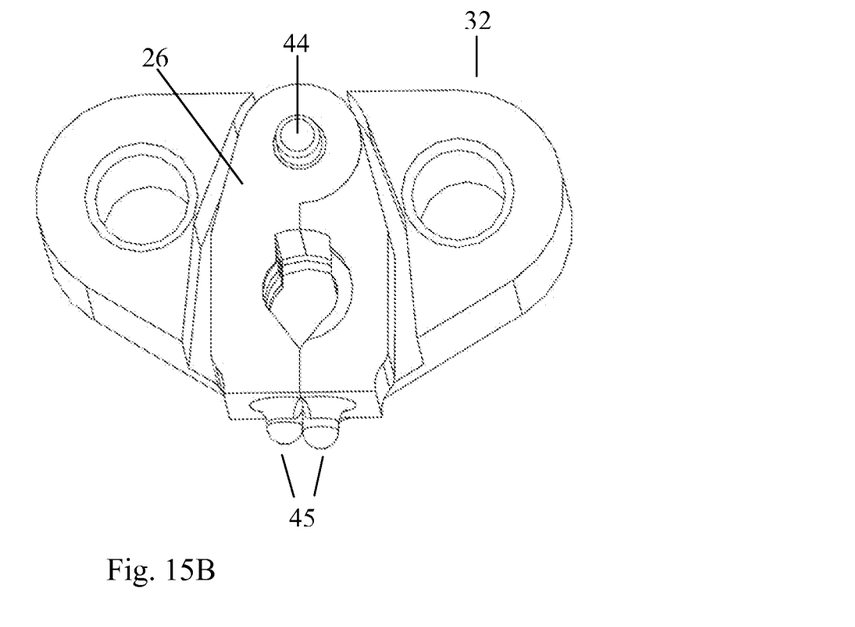
Figure 16:
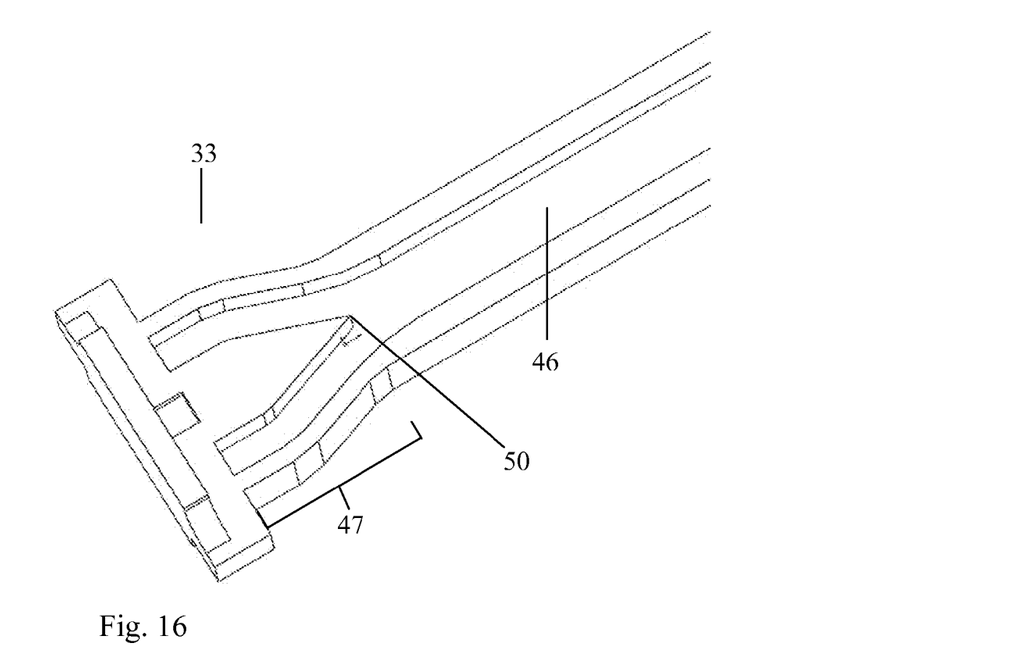
FIG. 16: illustrates the structure of the inner end of the spread bar (33) according to some embodiments of the present invention.

FIGS. 15A and B illustrate part of the releasing mechanism (R1) which comprises a split nut (26). The split nut can be in an opened (A) or closed (B) position. The split nut has a pivot (44) and two bulges (45) which are associated with spread bar 33. The split nut is opened by pushing aside the two bulges (45). FIG. 16 illustrates the spread bar (33) according to some embodiments of the present invention. The handle design includes channels cavities (46) creating a fork like shape (47). When the split nut is pushed against the splitting point (50) at the fork like shaped channels (47)—the bulges are pushed aside and the split nut is in its opened position.

According to some embodiments of the present invention, the split nut (26) (shown in FIGS. 15A and B) is located within the plunger base (32) and is composed of two parts which are connected to each other via a pivot connection (44). Each part of the split nut has a bulge (45) protruding from the plunger base (see the protruding bulges in FIGS. 18A and B). The bulges are spaced apart in the split nut "opened position" (FIG. 15A) or are positioned in proximity to one another in the split nut "closed position" (FIG. 15B). The spread bar (33) (FIG. 16) design has a narrow inner slide channel which splits into two channels (47). The bulges (45) of the split nut (26) are associated with the slide channel (46) of the spread bar (33) e.g. the bulges of the split nut can be situated inside the slide channel of the spread bar. In one embodiment, in the initial state of the device, the plunger base (32) (with the split nut within) is located close to the front end of the first housing element (28) and the two bulges (45) are located in the channels of the fork-like structure (47) spaced apart (see FIGS. 15A, 16 and 17). At this position of the bulges (45), the split nut is in an opened position, and the split nut is physically disconnected from the rotatable cylindrical threaded shaft (36). Pulling the handle (30) at this stage (for loading of the barrels) results in movement of the plunger base (32) and the plungers (27) in the direction V1. Prior to actuating the device, the spread bar (33) may be pushed back into the void of the first housing element (28), locating the bulges at the upper narrower end of the slide channel at a closed position. In the closed position of the split nut (26), pressing the actuating handle (20) causes rotational movement of the rotatable cylindrical threaded shaft (36), while advancing the split nut, the plunger base and the plungers in the direction V4 for dispensing the liquid components. When the bulges (45) reach the channels of the fork-like structure (47), the plungers are located within the emptied-syringe barrels (42) close to the front end of the second housing (1) and they are once again in a spaced position and thus the split nut is in its opened position.

Figure 17:
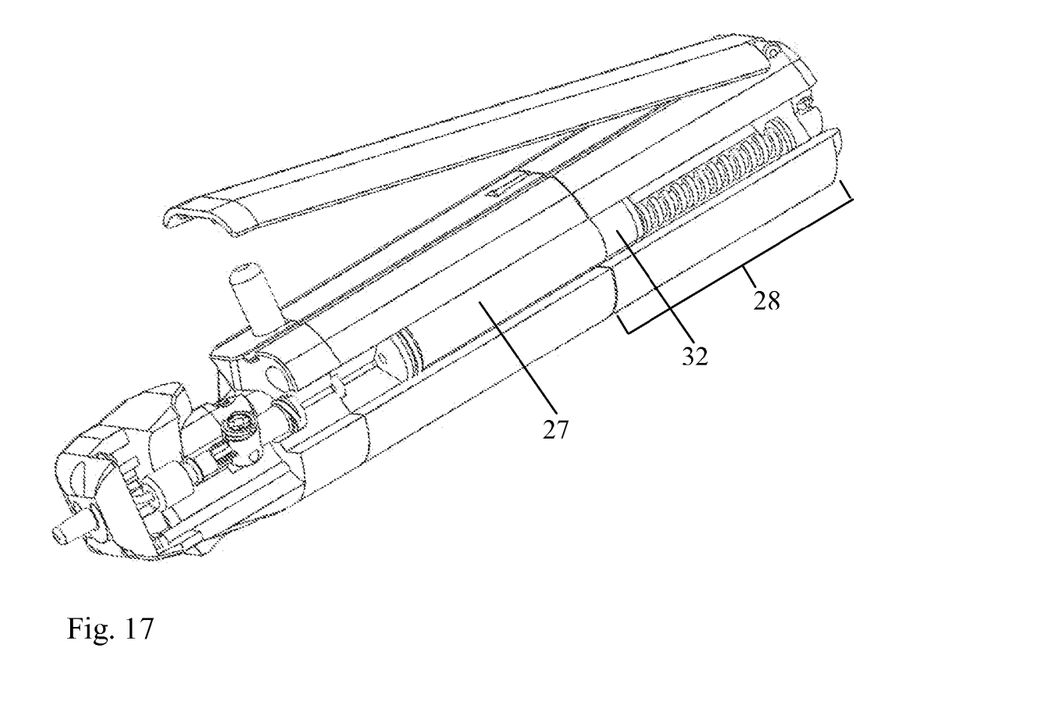
FIG. 17: illustrates an initial state of the device wherein the plunger base (32) is located close to the front end of the first housing (28) and the plungers (27) are located within the barrels according to some embodiments of the present invention.

FIG. 17 illustrates some of the inner parts of the device according to some embodiments of the present invention. The plungers (27) are positioned in their initial position at the second housing element (1) and the plunger base (32) is positioned in the front of the first housing element (28).

Figure 18A:
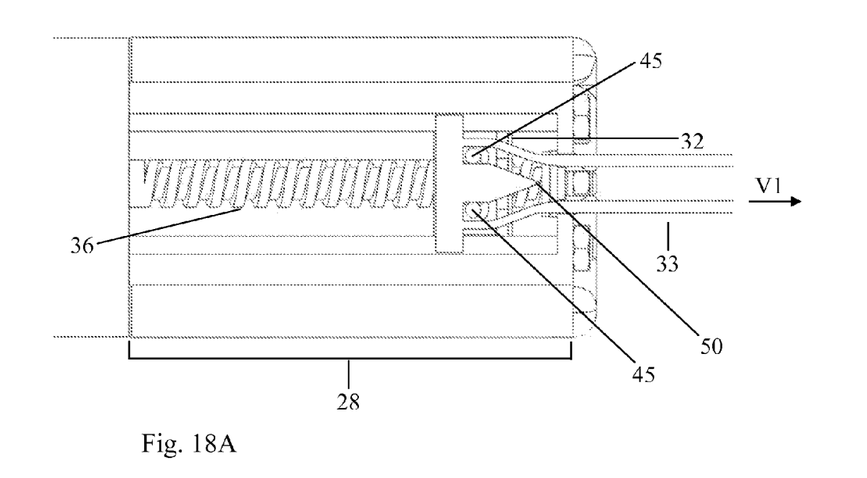
FIGS. 18A-18B: illustrate the split nut in an opened (A) and closed (B) position when situated in the channels of spread bar 33, illustrating the process of opening the split nut (26) according to embodiments of the present invention.
Figure 18B:
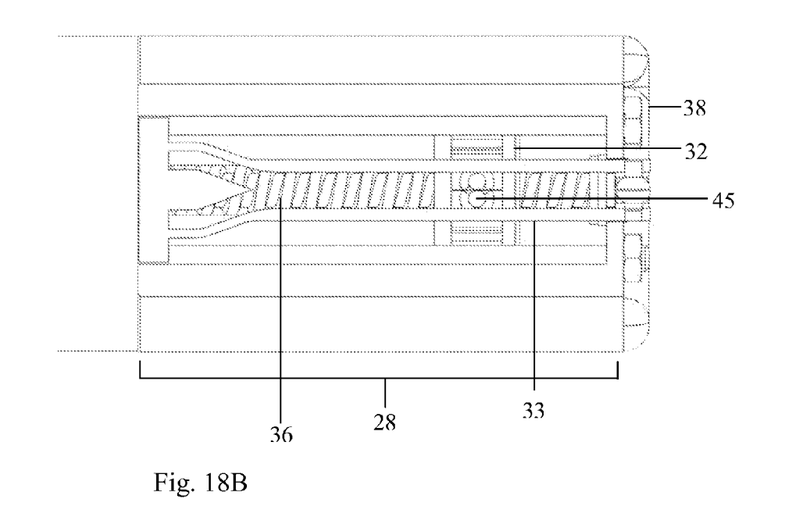

FIGS. 18A and B illustrate the association of the split nut with the spread bar (33). FIG. 18A illustrates the operation of the releasing mechanism, illustrating the split nut in an opened position disconnected from the cylindrical threaded shaft (36) and FIG. 18B illustrates the split nut in its closed position.

FIG. 18A depicts the open position where the bulges (45) are spaced apart, each bulge is located in a separate channel of the fork like structure (47). This position occurs when pulling the handle 30 backwards (in direction V1), the bulges (45) are stressed against the splitting point (50) of the fork like structure and the two bulges are spaced apart by the two channels, thus opening the split nut (26). FIG. 18B depicts the closed position, where the bulges (45) are located in proximity to one another. This position occurs when the two bulges are poisoned in the narrow section of the spread bar (33). According to some embodiments of the present invention, the releasing mechanism (R1) comprises a splitting element (50), such that when moving the splitting element along the barrel's axis during the loading process, the split nut is opened by the splitting element. According to some embodiments of the present invention: the operating sequence of the device is as follows:

In an initial state of the device, the plungers (27) are located within the barrels (42) close to the front end of the second housing (1) (see FIG. 6).

LOADING—In the first step, the spike cups (40) are installed on the fluid control device (6), and vials/reservoirs (41) are placed within the spike cups (40) (vials located within the spike cups are shown in FIG. 2). In one embodiment, the spike cups may comprise a protruding needle preferably adapted to puncture the vial's septum on the respective vial. The vials in the spike cups (40) are punctured by the protruding needle, enabling liquid flow from the vials and into the barrels (42) via the needle. Then, the handle (30) is pulled (see direction V1 in FIG. 1) in the opposite direction to the dispensing direction—pulling the spread bar (33) out from the inner space of the first housing (28) (see the extracted position of the spread bar (33) in FIG. 2). The spread bar (33) is connected to the plunger base (32) (see FIG. 7), hence pulling of the spread bar (33) moves the plungers (27) in the same direction V1, resulting in drawing of the fluid components from the vials (41) into the barrels (42). The fluid path during loading process of conveying fluids from the vials (41) into the barrels (42) is shown in FIG. 8. The loading mechanism is more specifically elaborated below. At the end of this step, the plungers (27) are partly located in the void of the first housing element (28) and partly at the void of the second housing element (1) (see FIG. 9).

At the next step, the spike cups (40) and the vials (41) are removed by rotating the spike cups (40) [thus allowing in a subsequent step (e.g. in a "liquid dispensing step", see below) flow of the fluids from the barrels (42), into the nozzles (9) positioned at the front end of the device and into the outlet of the device (39). This process is administrated by fluid control devices (6). The structure and function of each fluid control device and its use for loading the barrels of the device with the fluid components as well as for dispensing the fluid components are explained in WO9810703 which content is incorporated by reference].

According to one embodiment of the invention, once each of the barrels (42a and b) are filled with the fluid components, the spread bar (33) is pushed back into the first housing element (28) by the handle (30) which is then secured in its seat [on the back (38) of the first housing element (28)].

LIQUID DISPENSING—For dispensing the fluids, the user presses the actuating handle (20) down in direction V2, resulting in movement of the plungers (27) in direction V4 (the dispensing direction) into the barrels (42). The movement of the plungers (27) pushes the liquid through the fluid control device (6), to the nozzles (9), resulting, in each actuation of the handle, in dispensing a fixed and simultaneous dose of the two fluid components through the outlet of the device (39). The fluid path during actuation of the handle (20) is shown in FIGS. 9 and 10. The mechanism involved in dispensing of the liquid components is more specifically elaborated below.

More specifically, in one embodiment of the invention, the liquid dispensing process comprises the following steps: pressing the handle (20) in direction V2 which activates a motion conversion process which comprises the following actions: pushing the push slide (18) and rack gear (43) in the same direction V2, compressing spring 17, rotating the pinion gear (3) in direction V3, and a corresponding rotation of the rotatable cylindrical threaded shaft (36). The rotation of the rotatable cylindrical threaded shaft (36) results in a linear movement of split nut 26 in the direction V4. In one embodiment, the split nut (26) is located within the plunger base (32). Hence, movement of the split nut (26) in direction V4 (FIGS. 9 and 10) advances the plungers (27) in the same direction and results in dispensing of a fixed dose of the fluid components through the outlet of the device (39). According to some embodiments of the present invention, the motion conversion process comprises a linear motion of the push slide (18) in the direction V2 which is transformed into a rotational motion of the rack gear (3), the two crown gears (2A and B), and the rotatable cylindrical threaded shaft (36), all in the direction V3. This rotational motion is transferred back into a linear movement of the split nut (26), the plungers (27) and the plunger's head (37) in the direction V4 causing dispensing of the liquid components through the outlet of the device (39).

The dose administered at each actuation operation of the device (e.g. in each full movement of handle 20 in the direction V2) is determined by the pitch of the threaded structure of the rotatable cylindrical threaded shaft (36) and the diameter of the barrels (42).

According to one embodiment of the present invention, as the user releases the handle (20), the push slide (18) is moved in an upward direction V5 utilizing the energy stored in the compressed spring (17). In such an embodiment, the pinion gear (3) rotates in the direction V6. In order to prevent a corresponding rotation of the threaded shaft (36), and consequently movement of the split nut (26) and the plungers (27) in an unwanted opposite direction V1 during the liquid dispensing step, the two crown gears (2A and B) are designed in a unique shape and orientation. For example, engagement of the two crown gears occurs only when the pinion gear (3) rotates in the direction V3 (the direction which leads to movement of the plungers (27) in the dispensing direction V4). Rotation of the pinion gear (3) in the direction V6, results in "sliding" of the two crown gears upon one another, consequently preventing the movement of the threaded shaft (36) which remains static at this stage (thereby preventing movement of the plungers in a direction opposite to the dispensing direction at the dispensing step).

More specifically, according to some embodiments, the loading of the fluids into the barrels is carried out from an external connected vial or reservoir of liquids. The loading can be carried out prior to the actuating process e.g. by handle 20. Re-loading of the barrels with additional fluids can also be carried out after dispensing all the fluids from the barrels or when the barrels are completely empty. When loading the fluids, the pulling handle (30) and the spread bar (33) are pulled in direction V1, resulting in a linear movement of the plungers (27) in the same direction V1, and drawing of the fluid components from the vials (41) and into the barrels (42). In this step of loading, the split nut (26), which is attached to the piston base (32), moves in the same direction V1. The movement of the split nut (26) during the loading step in direction V1 is independent from the rotational motion of the rotatable cylindrical threaded shaft (36), since the split nut is in its opened position (the two bulges are located in the wider slide channel of the fork-like structure) and thus is physically disconnected from the rotatable cylindrical threaded shaft (36).

According to some embodiments of the present invention, the diameter of each barrel can be different, where the ratio between the diameters is designed to fit a required ratio between the liquid components.

Figure 1:
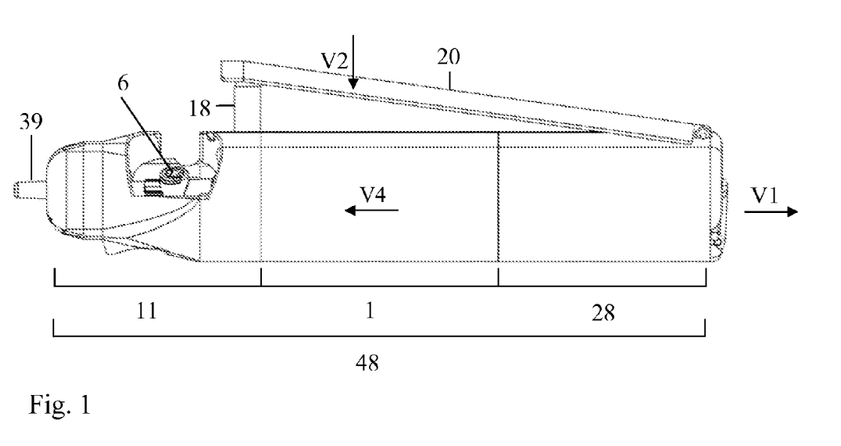
FIGS. 1-2: illustrate an external view of the device according to some embodiments of the present invention.
Figure 19:
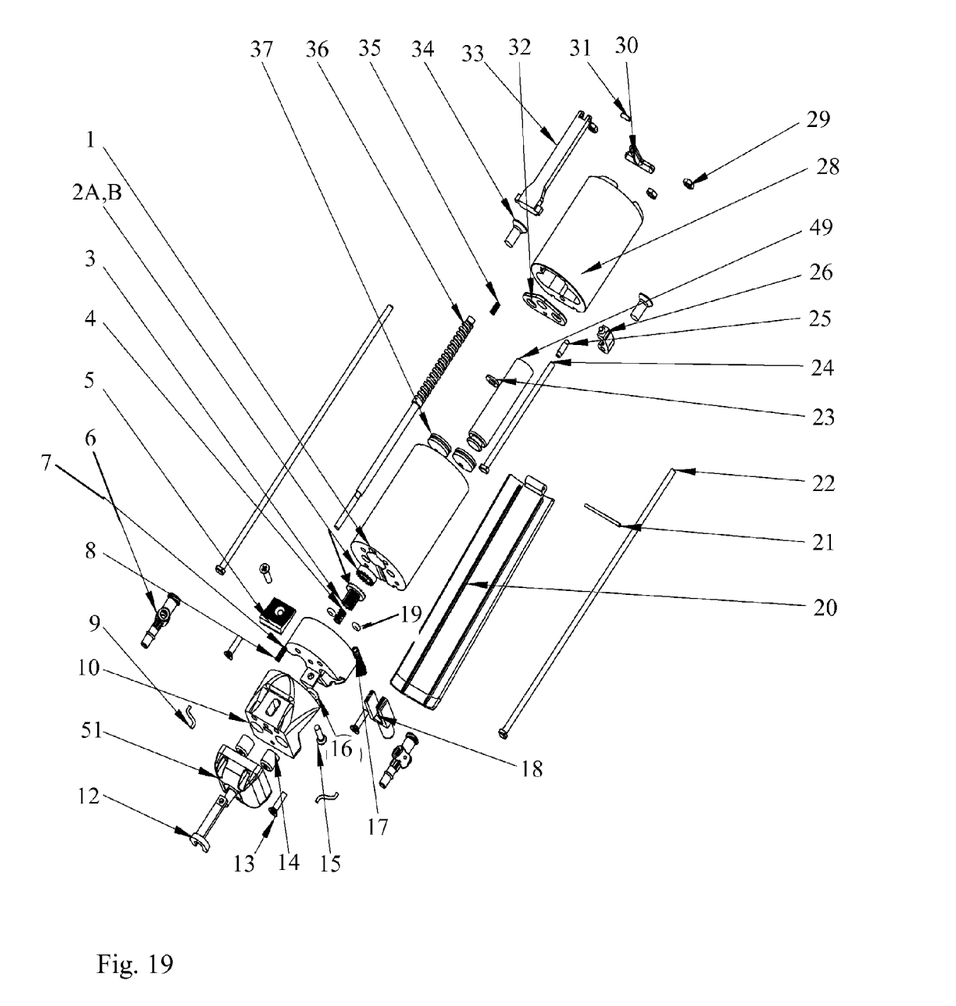
FIG. 19: illustrates an exploded view of the device according to some embodiments of the present invention.

An exploded view of the device as illustrated in FIGS. 1-2 is shown in FIG. 19. The device assembly may comprise the following parts: (28, 1, 11) housing elements constructing housing 48; (2A and B) two opposite crown gears; (3) pinion gear; (4) the spring of gear (3); (5) the button of the needle ejector; (6) fluid control device; (7) rear part of third housing element (11); (8) the spring of the needle ejector; (9) nozzle/tube/manifold; (10) part of third housing element (11); (51) front part of the third housing element (11); (12) needle ejector; (13) M3 screw; (14) bushing [an adaptor between the fluid control device (6) and tube (9)]; (15) M3 screw; (16) O ring, front; (17) spring of push slide 18; (18) push slide; (19) O ring, back; (20) actuating handle; (21) pin of the handle; (22) stud, long (connects parts 11, 1 and 28); (23) washer; (24) stud, short (connects parts 1 and 28); (26) split nut; (29) M3 nut; (30) pulling handle; (31) pin of the pulling handle; (32) plungers base; (33) spread bar; (34) screw of the plunger base; (36) rotatable cylindrical threaded shaft; (37) plunger's head; (43) rack structure of the push slide (18); (49) the body of the plungers Part 7, 10 and 51 assembles the third housing (11) seen in FIG. 1. Parts 49 and 37 construct (27) the plunger (see in FIG. 7).

In one embodiment of the invention, the washer 23 acts as a stopper of the (36) rotatable cylindrical threaded shaft, it protects housing 28, since housing 28 is made from plastic and the shaft is made from aluminum. The washer prevents the screw from indenting into the plastic. In one embodiment, the washer is made from steel. In one embodiment of the invention, except from parts 37, 19, and 16, which are made of rubber, all the other parts are made of metal or plastic materials.

The disclosure of applications, patents and publications, cited above, is hereby incorporated by reference.

The invention claimed is:

1. A device for dispensing a fixed dose of fluid, the device comprising:
at least one barrel;
at least one plunger at least partially enclosed within the barrel;
a motion conversion mechanism for transferring actuated pressure force applied outside the barrel into movement of the at least one plunger in a dispensing direction, wherein the motion conversion mechanism comprises at least one rotating gear, wherein the motion conversion mechanism comprises at least one rotatable cylindrical threaded shaft connected directly or indirectly to the at least one plunger; and
a releasing mechanism for disconnecting the plunger from the motion conversion mechanism, wherein at a released position the at least one plunger can move in a direction opposite to the dispensing direction, independent of a rotational movement of the at least one gear, and wherein the movement of the plunger in the opposite direction to the dispensing enables loading the fluid into the barrel, wherein the releasing mechanism comprises a split nut attached to the at least one plunger, wherein the split nut engages the cylindrical threaded shaft and rotates along the cylindrical threaded shaft and the operation of the releasing mechanism comprises opening the split nut to enable free movement of the plunger.

2. The device of claim 1, wherein the motion conversion mechanism further comprises at least one rack gear, and at least one pinion gear, wherein the releasing mechanism disconnects the plunger from the cylindrical threaded shaft.

3. The device of claim 2, wherein the releasing mechanism further comprises a splitting element, wherein the split nut is composed of two parts connected via a pivot and has an opened and closed position, such that when the splitting element is moved along the barrel axis during the loading, the split nut is opened by the splitting element.

4. The device of claim 3, wherein the splitting element is part of a bar having a fork-like channel structure, wherein the bar is connected to a pulling handle, wherein the split nut is composed of two parts connected via a pivot connection and the bar is associated with the two parts of the split nut such that the movement of the bar caused by pulling the handle pushes the split nut parts apart in the fork-like channel, thereby opening the split nut.

5. The device of claim 4, further comprising an actuating handle located outside the barrel and rack and pinion gears which convert a linear movement of the handle into the rotational movement of the cylindrical threaded shaft.

6. The device of claim 5, wherein at each actuation operation the fixed dose is determined by the pitch of the cylindrical threaded shaft and the diameter of the barrel.

7. The device of claim 6, wherein the rack gear is connected to the rotatable cylindrical threaded shaft by two opposite crown gears enabling rotation of the cylindrical threaded shaft only in one direction.

8. The device of claim 7, wherein the crown gears design forms small gaps between the gear's teeth preventing backwards movement of the plunger throughout the motion conversion mechanism operation.

9. A device for dispensing a fixed dose of fluid, the device comprising:
at least one barrel;
at least one plunger at least partially enclosed within the barrel;
a motion conversion mechanism for transferring actuated pressure force applied outside the barrel into movement of the at least one plunger in a dispensing direction, wherein the motion conversion mechanism comprises at least one rotating gear; and
a releasing mechanism for disconnecting the plunger from the motion conversion mechanism, wherein at a released position the at least one plunger can move in a direction opposite to the dispensing direction independent of a rotational movement of the at least one gear, wherein the movement of the plunger in the opposite direction enables loading the fluid into the barrel,
wherein the motion conversion mechanism comprises at least one rack gear, at least one pinion gear, and at least one rotatable cylindrical threaded shaft connected directly or indirectly to the at least one plunger, wherein the releasing mechanism disconnects the plunger from the cylindrical threaded shaft;

wherein the releasing mechanism comprises a split nut attached to the at least one plunger and engages the cylindrical threaded shaft, wherein the split nut rotates along the cylindrical threaded shaft and the operation of the releasing mechanism comprises opening the split nut to enable free movement of the plunger in the opposite direction.

10. A system for dispensing a fixed dose of two fluids and creating a mixed composition of the two fluids, the system comprising:

a housing enclosing two cylindrical cavities forming two barrels;

two plungers at least partially enclosed within the barrels;

a motion conversion mechanism for transferring actuated pressure force applied outside the housing into movement of the plungers in a dispensing direction, wherein the motion conversion mechanism comprises at least one rack gear, at least one pinion gear, and at least one rotatable cylindrical threaded shaft connected with the two plungers;

a releasing mechanism for disconnecting the two plungers from the rotatable cylindrical threaded shaft, wherein at a released position the plungers can move in an opposite direction to the dispensing direction independent of the rotational movement of the motion conversion mechanism; and two nozzles for each barrel connected to an outlet opening of the system, wherein the fluids pass from the barrels through the nozzles into the outlet opening of the system.

11. The system of claim 10, wherein the system comprises a split nut attached to the two plungers and engages the cylindrical threaded shaft, wherein the split nut rotates along the rotatable cylindrical threaded shaft and the operation of the releasing mechanism comprises opening the split nut to enable free movement of the plungers.

12. The system of claim 11, wherein the releasing mechanism comprises a pulling handle connected to a bar having fork-like channel structure, wherein the split nut is composed of two parts connected via a pivot connection, and the bar is associated with the two parts of the split nut such that the movement of the bar caused by pulling the handle pushes the split nut parts apart in the fork-like channel, thereby opening the split nut.

13. The system of claim 12, further comprising an actuating handle located outside the housing, and rack and pinion gears which convert a linear movement of the handle into the rotational movement of the cylindrical threaded shaft.

14. The system of claim 13, wherein at each actuation operation the fixed dose is determined by the pitch of the cylindrical threaded shaft and the diameter of the barrels.

15. The system of claim 14, wherein the rack and pinion gears are connected to the rotatable threaded shaft by two opposite crown gears enabling rotation of the cylindrical threaded shaft only in one direction.

16. The system of claim 15, wherein the crown gears design forms small gaps between the gear teeth preventing backwards movement of the plunger throughout the motion conversion mechanism operation.

17. A method for loading and dispensing a fluid, the method comprising the steps of:

moving an at least one plunger through an at least one barrel in a dispensing direction by transforming pressure applied outside the at least one barrel into a linear movement of the at least one plunger in the dispensing direction, the transformation achieved through a rotational movement of a motion conversion mechanism, wherein the rotational movement comprises rotation of a split nut along a rotatable cylindrical threaded shaft, wherein the split nut is directly or indirectly connected to the at least one plunger and the cylindrical threaded shaft is part of the motion conversion mechanism, disconnecting the at least one plunger from the motion conversion mechanism for moving the at least one plunger in a direction opposite to the dispensing direction independent of the rotational movement of the motion conversion mechanism, wherein the movement of the at least one plunger in the opposite direction enables loading the fluid from a connected reservoir into the at least one barrel.

18. The method of claim 17, wherein the disconnecting comprises opening the split nut to enable free movement of the at least one plunger for loading the at least one barrel with the fluid.

19. The method of claim 18, further comprising the step of closing the split nut to reconnect the at least one plunger to the cylindrical threaded shaft for enabling the dispensing operation.

20. The method of claim 18, wherein the opening and loading further comprises pulling a handle connected to a bar having a fork-like channel structure, wherein the split nut is composed of two parts connected via a pivot connection and the fork-like channel structure is associated with the two parts of the split nut such that the movement of the fork-like channels structure, caused by pulling the handle, pushes the parts apart, thereby opening the split nut.

21. The method of claim 17, wherein the rotational movement is achieved by converting a linear movement of a handle into the rotational movement using a rack, and pinion gears.

22. The method of claim 21, wherein the rack and pinion gears are connected to the rotatable threaded shaft by two opposite crown gears enabling rotation only in one direction.

23. The method of claim 17, wherein the dispensing is selected from the group consisting of injecting, spraying and dripping.

24. The system of claim 10, wherein the ratio between the diameters of the two barrels is correlated to the required ratio between the two fluids.

25. The device of claim 4, wherein the split nut has a pair of bulges attached at the end of each part of the split nut, the bulges are designed to slide in the channels of the spread bar for opening or closing the split nut.

26. A device for dispensing a liquid comprising: at least one barrel; at least one plunger which can be disposed within the at least one barrel; a rotatable cylindrical threaded shaft; a split nut connected directly or indirectly to the at least one plunger and having an opened position and a closed position, wherein the split nut engages the threaded shaft in the closed position and is disengaged from the threaded shaft in the opened position, when the split nut is in the closed position, rotation of the threaded shaft translates into a linear movement of the split nut and the at least one plunger in a dispensing direction, and when the split nut is in the opened position it disengages from the threaded shaft, thereby allowing the at least one plunger to move opposite to the dispensing direction.

27. The system according to claim 10, wherein the two fluids are a thrombin component and a fibrinogen component.

* * * * *